(12) United States Patent
Tsivkin

(10) Patent No.: US 6,258,348 B1
(45) Date of Patent: Jul. 10, 2001

(54) HAIR CONDITIONING FORMULATION FOR MENDING SPLIT ENDS

(75) Inventor: Irina Tsivkin, Stamford, CT (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/384,620

(22) Filed: Aug. 27, 1999

(51) Int. Cl.[7] .................................. A61K 7/06; A61K 7/08
(52) U.S. Cl. ................... 424/70.12; 424/70.1; 424/70.11; 424/70.12; 424/70.27; 424/70.28
(58) Field of Search ................................... 424/401, 70.1, 424/70.11, 70.12, 70.27, 70.28

(56) References Cited

U.S. PATENT DOCUMENTS 4,900,545 * 2/1990 Wisotzki et al. .
6,120,753 * 9/2000 Vinski et al. .

* cited by examiner

*Primary Examiner*—Thurman K. Page
*Assistant Examiner*—Brian K. Seidleck
(74) *Attorney, Agent, or Firm*—Carmella A. O'Gorman

(57) ABSTRACT

The invention provides compositions for mending split ends of keratinous fibers, particularly human hair. The compositions of the present invention contain guar, a betaine based polyurethane surfactant and a silicone polyurethane.

10 Claims, No Drawings

HAIR CONDITIONING FORMULATION FOR MENDING SPLIT ENDS

FIELD OF THE INVENTION

The present invention concerns a hair formulation containing a polysaccharide gum in combination with a betaine based polyurethane surfactant and a polyurethane silicone. The formulation is useful in repairing split ends.

BACKGROUND OF THE INVENTION

The problem of mechanical damage to hair can be approached cosmetically from two points of view: prevention—minimize the tangling and abrasive effects of handling the hair providing lubrication to reduce fiber friction, and repair—mend existing damage by depositing substances that will restore axial cohesion to splits or "fill in" areas of shaft damage. Shampooing is the cosmetic process to which the hair is exposed most frequently. The conditioner is a popular method to make combing easier, thus reducing mechanical damage. While both shampoos and conditioners that effectively prevent damage are known, there are no products in this category that effectively repair split ends. There are materials that are known to give hair improved dry combing and keep split ends closed. Cationic polymers (guars and other polysaccharides), due to their affinity to protein substrates, are known for having good wetting and combing properties. Sorbed polymers are effective in mending split ends, the split remaining mended under further abrasion of the dried fiber. Proteins have been used for many years in hair care products for their substantivity and mending effects.

U.S. Pat. No. 5,147,635 (Sep. 15, 1992; Inventors: J. Jachowicz and C. Ramireddy) discloses one-step cleaning and conditioning compositions, containing at least one urethane and urea group, which are derived from isocyanatoethyl (meth) acrylates or meth acrylic acids, that have good conditioning properties and can be formulated in the presence of a mixture of amphoteric and anionic surfactants. The invention deals with novel cationic polyelectrolytic materials, as well as their production, compositions containing these materials and methods of using the composition.

U.S. Pat. No. 4,900,545 (Feb. 13, 1990; Inventors: Wisotzki et al.) discloses a hair split end regeneration composition containing panthenol, saccharides, polynyvylperrolidone and triolemulsion. The disclosed composition for the regeneration of hair split ends is in an aqueous or aqueous/alcoholic solution.

Heretofore, a composition for the repair or regeneration of hair split-ends based on a guar, a betaine based polyurethane surfactant, and a silicone polyurethane has been unknown.

BRIEF SUMMARY OF THE INVENTION

This invention relates to a hair conditioning formulation that provides mending of the split ends of keratinous fibers, especially human hair. The composition of the present invention is an aqueous hair conditioning composition comprising:

A) guar gum;

B) a betaine based polyurethane surfactant; and

C) a silicone polyurethane.

The three components (i.e., A, B, and C) are present in the composition amounts effective to mend split ends of human hair to a degree greater than the same composition with only two of the three components. This invention is especially beneficial for colored, bleached, or relaxed hair.

DETAILED DESCRIPTION OF THE INVENTION

The present invention provides aqueous hair care and treatment compositions comprising a guar, preferably an amphoteric or cationic guar (e.g., guar hydroxypropyl trimonium chloride, CTFA nomenclature), a betaine based polyurethane surfactant, and a silicone polyurethane.

In general, the guar component of the compositions in accordance with the present invention is an amphoteric guar gum or a cationic derivative of guar gum or locust bean gum. Cationic guars are disclosed in, for example, Japanese Patent No. 5345708, U.S. Pat. No. 4,557,928 and U.S. Pat. No. 4,387,090, the disclosures of which are incorporated herein by reference in their entirety. Amphoteric guars are available, for example, from Meyhall Chemicals under the trademark "Meyprobond 120" and from National Starch and Chemical. Other amphoteric and cationic guar gums which may be used in connection with the present invention, are commercially available from various sources, including Henkel Corporation (Minneapolis, Minn., U.S.A.) and Celanese Plastics & Specialities Company (Louisville, Ky., U.S.A.) under the trade marks GENDRIV and CELBOND. Chemical derivatization of guar is carried out mainly through the hydroxyl groups of the galactose or the mannose units of guar of which primary (6 and 6') hydroxyls are the most reactive. Preferred substituents for amphoteric guar are —$OCH_2COONa$ and —$OCH_2CHOHCH_2$—$N(CH_3)_3Cl$. Suitable guars useful herein are polygalactomannans containing two mannose units with a glycoside linkage and a galactose unit attached to one of the hydroxyl groups of the mannose units.

Synthesis of amphoteric guar useful herein can be prepared according to the following scheme:

Wherein SMCA is sodium monochloroacetate.

The degree of substitution (DS) is defined as the ratio of the number of substituted hydroxyls in the sugar (galatose/mannose) to the average number of hydroxyls available per repeat unit. The type and the extent of derivatization largely depend on the process as well as the reagents chosen for the reaction.

A preferred amphoteric guar useful herein has repeating units as follows:

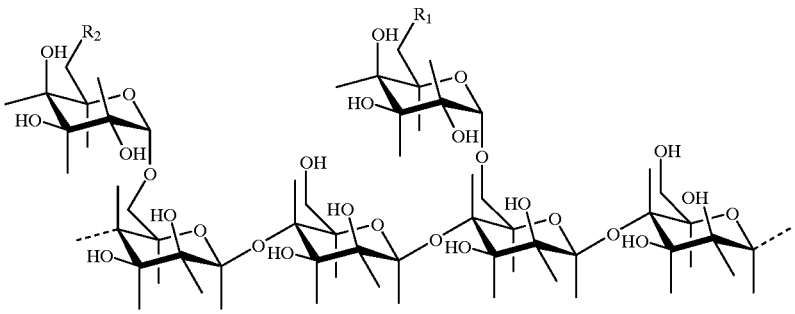

wherein $R_1$ is —$OCH_2COONa$ and $R2$ is —$OCH_2CHOHCH_2$—$N^+(CH_3)_3$ CL.

To prepare cationic guars, the hydroxyl groups are reacted with certain reactive quaternary ammonium compounds to obtain the cationic derivative.

The quaternary ammonium compounds suitable for preparing the cationic gum derivatives of the present invention have the structure:

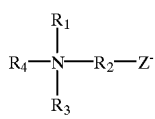

wherein $R_1$, $R_2$ and $R_3$ are alkyl, aryl and substituted alkyl and aryl groups; $R_4$ is selected from the group consisting of epoxyalkyl and halohydrin, and $Z^-$ is an anion, e.g., $Cl^-$, $Br^-$, $I^{31}$ and $HSO_4^-$. Suitable epoxyalkyl groups have the structure:

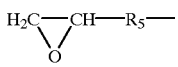

Suitable halohydrins have the structure:

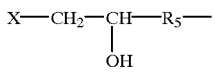

wherein $R_5$ is a divalent alkylene of 1 to 3 carbons, and X is a halogen.

Particularly preferred is the compound 3-(trimethylamino)-2-hydroxypropyl guar chloride which has the structure:

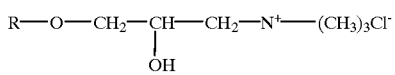

wherein R is the polygalactomannan molecule based on guar, and is sold as Cosmedia Guar 216N by Henkel Corporation.

Particularly preferred for use in the compositions of the present invention are quatemary ammonium derivatives of hydroxypropyl guar, such as guar hydroxypropyltrimonium chloride, which is exemplified by the JAGUAR products commercially available from Rhodia. The most preferred cationic guar has the CTFA designation: guarhydroxypropyltrimonium chloride (Trade Name: Jaguar C-13S).

A preferred amphoteric guar useful herein has the CTFA designation: carboxymethyl guar hydroxypropyltrimonium chloride available from National Starch and Chemical Company.

In accordance with the present invention, the aqueous hair compositions as described contain one or more of the above-described amphoteric guars and/or cationic guars, in combination with the betaine based polyurethane surfactant and silicone polyurethane, in an amount effective to mend or repair split ends of human hair. More particularly, the guar(s) are typically present in the compositions of the present invention in, an amount of from about 0.05% to about 5%, preferably, about 0.1% to about 4%, more preferably, about 0.2% to about 3% by weight, and most preferably about 0.25% to about 2%, based on the total weight of the composition. It will be appreciated that quantities of guar different from those specifically recited herein can be used, depending upon the other ingredients in the formulation and the desired effect of the formulation. In such instances, the actual amounts for use can be determined by routine testing.

It is also to be understood that unless otherwise specified herein, all components of the compositions of the present invention are present in % by weight, based on the total weight of the composition.

The betaine based polyurethane surfactant is amphoteric by virtue of the betaine moiety. The betaine based polyurethane surfactants can be prepared by conventional techniques known in the art.

The term "betaine based polyurethane surfactant" means a surfactant having 2 or more preferably 3 or more, for example 2-20, 2-10, 3-20, or 3-10 moieties of the formula:

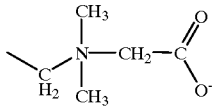

and 2 or more, preferably 3 or more, for example 2-20, 2-10, 3-20, or 3–10 urethane moieties of the formula:

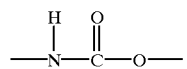

The betaine based polyurethane surfactant may also contain additional moieties such as hydrocarbyl moieties, e.g., straight or branched chain alkyl group, straight or branched chain alkenyl groups, cycloalkyl groups; amido groups, and the like.

A preferred betaine based polyurethane is a ricinoleamidopropyl urethane betaine. A specific preferred betaine based polyurethane surfactant is bis (ricinoleamidopropyl dimethylamine polymer/isophorone diisocyanate N-carboxymethyl-N,N-dimethyl) hydroxide inner salt. The structure of this betaine based polyurethane surfactant is as follows:

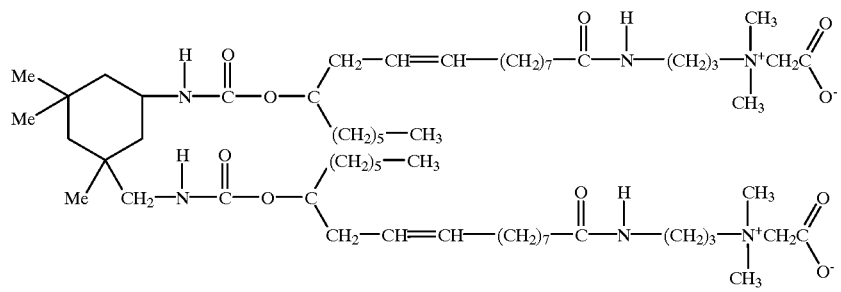

A more preferred betaine based polyurethane surfactant comprises 2 or more eferably 3 or more and up to 10 or 20 of the following repeating units:

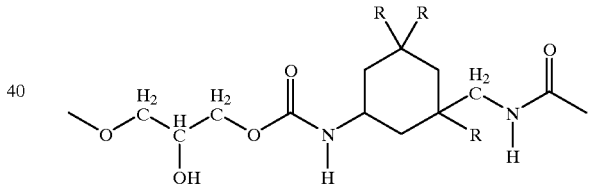

wherein each R group is, independently, H or a $C_1$–$C_4$ alkyl, preferably methyl.

Another preferred betaine based polyurethane surfactant (Trade Name: Foamtaine PPI-RC, available from Alzo, Inc., Matewan, N.J.). has the structure:

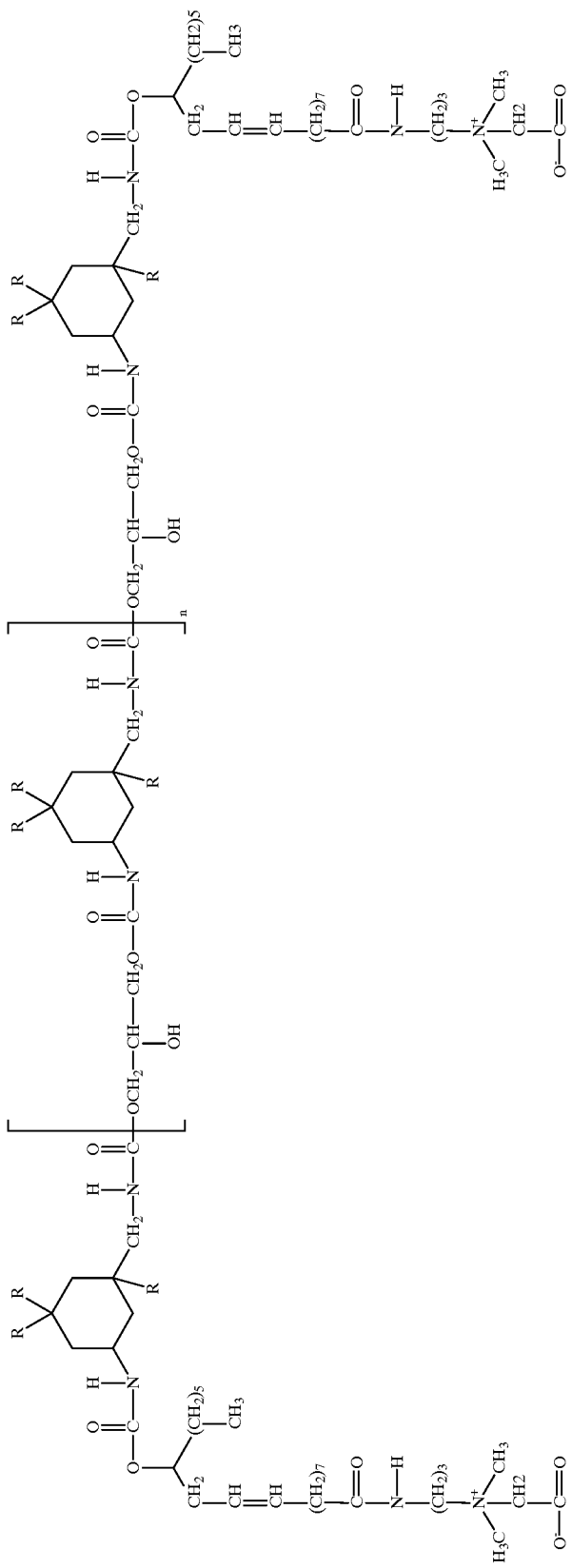

wherein n is a positive integer of 2 or more, preferably 3 or more such as 2-20, 2-10, 3-20 or 3-10; and each R is, independently, H or a $C_1$–$C_4$ alkyl group, preferably methyl.

The preferred betaine based polyurethane surfactant can be prepared according to the following procedure:

Step 1)—Procedure for the Amido-Amine:
a) To a clean dry 2 liter flask, add one mole of Castor Oil. With a vacuum of 27 inches, dry the castor oil by raising the temperature to 125° C.
b) Cool the batch down to approximately 35° C. and add 3.3 moles of dimethylaminopropyl amine. Bring to reflux under approximately 10 pounds of pressure and hold for 30 minutes.
c) Cool the batch to approximately 60° C. and with a slight vacuum, strip. out excess dimethylaminopropyl amine. Continue this stripping operation until an alkali value of 145–150 has been achieved.

Step 2)—Procedure for the Polyurethane Reaction:
Take 2 moles of the ricinoleamidopropyldimethyl amine prepared in Step 1) into a clean dry flask. Bring the temperature up to 80–110° C. with agitation and under a nitrogen blanket. Slowly drop in 1 mole of isophorone diisocyanate over a 2 hour period and follow the reaction with infrared until the isocyanate peak in no longer evident.

Step 3)—Final Procedure for the Betaine based polyurethane surfactant:
a) Into a 2 liter flask, introduce 708 grams of polyurethane of ricinoleamidopropyldimethyl amine prepared in Step 2) and bring to a temperature of 70° C.
b) Into a separate 3 liter flask, introduce 150 grams of sodium monochloracetate (SMCA) containing 1080 grams of deionized water.
c) Bring the SMCA/deionized water solution to a temperature of 50° C. and add the polyurethane of n-ricinoleamidopropyldimethyl amine. (An emulsion will initially form {water in oil}).
d) Raise the temperature to approximately 85–90° C. and continue to hold until clarity is achieved.
e) Continue to stir until a pH of 5–7 on as-is-basis is reached.

In accordance with the present invention, the aqueous hair compositions as described contain one or more of the above-described betaine based polyurethane surfactants, in combination with the guar and silicone polyurethane, in an amount effective to mend or repair split ends of human hair. More particularly, the betaine based polyurethane surfactant (s) are typically present in the compositions of the present invention in an amount of from about 0.1% to about 30%, preferably, about 0.5% to about 20%, more preferably, about 0.75% to about 10% by weight, and most preferably about 0.25% to about 3.5%, based on the total weight of the composition. It will be appreciated that quantities of betaine based polyurethane surfactant different from those specifically recited herein can be used, depending upon the other ingredients in the formulation and the desired effect of the formulation. In such instances, the actual amounts for use can be determined by routine testing.

The silicone polyurethane can be prepared by conventional techniques known in the polymer art using polymerization techniques starting with desired monomers. Many suitable silicone polyurethanes are commercially available.

The silicone polyurethane can be either water soluble or water insoluble. The silicone moiety of the silicone polyurethane is a siloxane, more specifically, moieties such as polyalkyl or polyaryl siloxanes with the following structure:

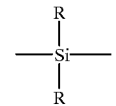

wherein each R is, independently, alkyl or aryl. The alkyl or aryl groups substituted on the siloxane chain (R) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on the hair.

The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. The silicone polyurethane can be a polyalkylene oxide poly di $C_1$–$C_4$ alkyl or poly diphenyl siloxane with isophorone diisocyanate. The polyalkylene moiety is preferably polyethylene glycol (PEG) or polypropylene glycol (PPG). It is also preferred that the polydialkyl siloxane moiety is polydimethyl siloxane. A preferred water-soluble silicone polyurethane is polydimethyl siloxane—PEG ether/isophorone diisocyanate copolymer (Trade name: Polyderm PPI-SI-WS, available from Alzo, Inc.). A preferred water insoluble silicone polyurethane is polydimethyl siloxane—PPG ether/isophorone diisocyanate copolymer (Trade name: Polyderm PPI-SI-WI, available from Alzo, Inc.). Another silicone polyurethane useful herein is a dimethiconol/isophorone diisocyanate copolymer (Tradename: Polyderm SI, available from Alzo, Inc.). The molecular weights of the silicone polyurethane can vary widely, e.g., about 2000 to about 10,000,000, preferably about 5,000 to about 1,000,000. A preferred silicone polyurethane has the structure:

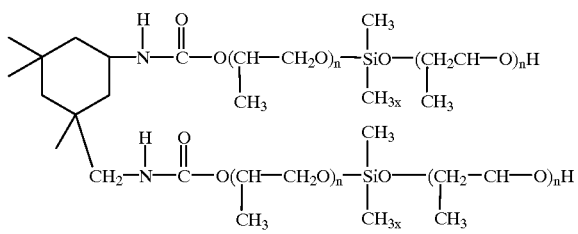

wherein x and n are positives integers, for example of 1 to 10,000, preferably 1 to 5,000, more preferably 1 to 1,000.

In accordance with the present invention, the aqueous hair compositions as described contain one or more of the above-described silicone polyurethanes, in combination with the betaine based polyurethane surfactant and guar, in an amount effective to mend or repair split ends of human hair. More particularly, the silicone polyurethane(s) are typically present in the compositions of the present invention in an amount of from about 0.1% to about 10%, preferably, about 0.5% to about 5%, more preferably, about 0.75% to about 3% by weight, and most preferably about 0.75% to about 2%, based on the total weight of the composition. It will be appreciated that quantities of polyurethane siloxane different from those specifically recited herein can be used, depending upon the other ingredients in the formulation and the desired effect of the formulation. In such instances, the actual amounts for use can be determined by routine testing.

For convenient, singular terms for the various components of the composition of the invention are used herein; however, it should be noted that mixtures of two or more of a specific component are contemplated to be within the scope of the invention; for example, the term "a silicone polyurethane" can mean either a single silicone polyurethane or a mixture of two or more different silicone polyurethanes.

The aqueous compositions of the present invention can be formulated into a wide variety of product types, generally as a solution or emulsion, for example, creams. Gels can also be formulated. In a shampoo base the formulation will provide desirable cleansing and foaming properties of a shampoo and the detangling and conditioning properties of a cream rinse or leave in product along with mending split ends. In a rinse-off or leave in conditioner base, the invention will provide excellent conditioning and repair of split ends.

Water is generally present in the compositions an amount such as is typically employed in compositions of this type; usually, such amounts are about 20% to 90%, and frequently, about 30% to 80%.

Also formulated in the compositions of the present invention can be one or more additional or auxiliary surfactants that function as detergents to clean the hair. Conventional surfactants such as anionic, cationic and amphoteric surfactants can be used in the detergent system. A detailed listing of suitable surfactants for the compositions herein can be found in U.S. Pat. No. 4,557,853, to Collins, issued Dec. 10, 1985, which is incorporated by reference herein. Commercial sources of such surfactants can be found in McCutcheon's EMULSIFIERS AND DETERGENTS, North American Edition, 1984, McCutcheon Division, MC Publishing Company, also incorporated herein by reference. The amount of additional surfactant can be from about 1% to about 70%, more typically about 2% to about 50%. Preferred surfactants for use in the present compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and cocoamphocarboxyglycinate. The most preferred of the optional surfactants for use herein are ammonium laureth sulfate and sodium laureth sulfate.

Secondary or auxiliary conditioning agents in addition to the guar, silicone polyurethane and betaine based polyurethane surfactant can also be formulated into the compositions of the present invention in amounts conventionally used for these reagents. Such auxiliary conditioning agents include those reagents or products which are typically employed in such compositions, nonlimiting examples of which include, but are not limited to, quaternary ammonium compounds, amines, ethyl sulfates and other cationic polymers. Among the quaternary ammonium compounds suitable for use are quaternary ammonium hydroxides, such as methyl triethanol ammonium hydroxide and tetraethyl ammonium hydroxide. Preferred auxiliary conditioning agents include polyquaternium 10 or benhentrimonium methosulfate. In general, auxiliary conditioning agents, when used, are present in amounts of about 0.1% to about 3.0%, preferably, about 0.5% to about 2.0%.

The compositions of the present invention may also contain optional ingredients which improve the elegance of the final products, as set forth below. In general, these additional components, and other suitable additives, as desired, provide cosmetically acceptable vehicles for the compositions of the invention and are present at levels which are effective to provide the components' intended functions.

One or more emollients and humectants are generally employed in compositions of this type in amounts typically used in such compositions. Examples of suitable emollients for use in accordance with the present invention include, but are not limited to, mineral oil and petrolatum. Other emollients may include cetyl or stearyl alcohol, paraffin or lanolin alcohol. Emollients are generally employed in the compositions of the present invention at about 5% to about 45%, preferably, about 7.5% to about 40%, by weight. Examples of suitable humectants include, but are not limited to, propylene glycol, hexylene glycol, glycerin and sorbitol. As a general guide, humectants can be present in such compositions in amounts of about 1% to about 20%, preferably, about 4% to about 10%.

One or more emulsifying agents are also generally present in the compositions of this invention in amounts typically employed in such compositions. Emulsifiers typically provide dispersion and suspension of the components, and render a creamy and lubricous consistency to the composition. Nonlimiting examples of emulsifying agents suitable for use include alkoxylated alcohols and fatty alcohols, such as stearyl, cetyl and cetearyl alcohols, ethoxylated sorbitan esters, ethoxylated lanolin and derivatives thereof As a general guide, mulsifiers can be used in amounts of about 1% to about 16%, preferably, about 2% to about 12%, and more preferably, about 8% to about 10%.

Opacifying agents are conventionally used in cream compositions. Suitable opacifying agents are the higher alcohols, such as stearyl and cetyl alcohol, and the higher acids, such as behenic acid. Sodium chloride and sodium sulfate can also be used as opacifying aids, when used in concentrations that do not cause gelation. Alkaline earth metal fatty acid soaps, such as calcium stearate and magnesium stearate, are also suitable. Magnesium silicates are also useful for this purpose. Opacifying agents are typically present in an amount of from about 0.1% to about 10%, preferably, from about 0.5% to about 5%.

Thickening agents increase the viscosity of a hair-related product. Suitable materials are natural gums such as tragacenth, xanthan, acacia and locus bean; and synthetic gums such as hydroxypropylcellulose and methyl cellulose. Polyvinyl alcohols can also be used. Alkanolamides, "super" amides and the glycol or glycerol stearates may also be used. Thickening agents are present in an amount to provide the desired viscosity. Amounts typically employed are from about 0.1% to about 10%, preferably, from about 0.1% to about 10%. The final viscosity of the product should be such that it can be applied to hair and easily distributed therethrough without dripping.

Other optional additives can include conventional additives such as foam stabilizers; viscosity builders; preservatives; sequestrates; antioxidants, such as sodium sulfite; chealating agents such as EDTA; suspending agents; fragrances or perfumes; herbals; sunscreens; and pH control agents, such as citric acid, each of which is present in an amount, usually less than 5%, effective to provide its intended function. An antidandruff component, e.g., selenium sulfide, may also be included at an effective level.

Advantages of the present compositions over prior art split ends repair systems include:

the composition is versatile, i.e., it works not only in a cream rinse or leave in system, but in a shampoo base as well, the surfactant system in a shampoo base is not limited to a certain class of surfactant, and the composition could be used as 2-in-1 system, (shampoo and conditioner in one).

The composition of the invention can be used as a regular shampoo and after shampooing is rinsed off completely. The exact mechanism of action to repair split ends and the method of attachment of the composition of the invention to the hair are not fully known. Although it is not intended to be bound by any particular mechanism or theory, it is believed that a complex of the betaine based polyurethane surfactant, silicone polyurethane and/or guar forms and plates out during contact with the hair, e.g., shampooing, and physically attaches itself to the certain sides on the hair shafts (e.g., to the split ends that are negatively charged). Sufficient amounts of the complex remain on the hair shafts after thorough rinsing to "fill in" the damaged split end and reduce tangles.

The present invention is also directed to a method for repairing split ends of hair comprising contacting hair with split ends with the composition of the invention followed by rinsing the hair with water.

The following examples are to illustrate the invention but should not be interpreted as a limitation thereon.

EXAMPLE 1

Hair Split End Repair with Betaine Based Polyurethane Surfactant, Silicone Polyurethane and Amphoteric Guar Objective The objective of this study is to evaluate the effect of the three ingredients that are incorporated in the shampoo based system. These ingredients are:

Amphoteric Guar or Cationic Guar from National Starch & Chemical Company or Rhodia, respectively, @0.25%

Polyderm PPI-SI-WS @1.00%

Foamtaine PPI-RC @3.00% Polyderm PPI-SI-WS (water-soluble) & Foamtaine PPI-RC are supplied by Alzo, Sayreville, N.J.

Six prototype formulations are prepared to conduct the experiment, which contain different combinations of the above ingredients:

TABLE 1

|  | Sample 1 | Sample 2 | Sample 3 | Sample 4 | Sample 5 | Sample 6 |
|---|---|---|---|---|---|---|
| GUAR (NS) | 0.2500 | 0.25 | 0.25 | 0.00 | 0.25 | 0.00 |
| Foamtaine PPI-RC | 0.00 | 3.00 | 0.00 | 0.00 | 3.00 | 3.00 |
| Polyderm PPI-SI-WS | 0.00 | 0.00 | 1.00 | 0.00 | 1.00 | 1.00 |
| Jaguar C-13S (Rhodia) | 0.00 | 0.00 | 0.00 | 000 | 0.00 | 0.25 |

Each of these formulas is tested on 2 tresses. Tresses are prepared from Caucasian dark brown hair provided by International Hair Importers and Products. Ten split end hair fibers are chosen and attached to a singe tab tress.

Procedure 0.5 cc of the corresponding prototype formula is applied to the tress and shampooed for thirty seconds, then rinsed with water for thirty seconds, and, finally, left to air dry. A total of two shampoos are performed for each tress.

Split end repair is evaluated under a magnifying glass. The amount of hair fibers mended have been calculated per each tress and averaged. Table 2. Displays formulation numbers, content of the prototype tested, and the percentage of hair fibers mended after the treatments.

TABLE 2

| SPLIT ENDS REPAIR WITH 2-IN-1 CONDITIONING SHAMPOO | | | | | |
|---|---|---|---|---|---|
| Ingredient Name | Sample 1 | Sample 2 | Sample 3 | Sample 4 | Sample 5 |
| Water | 43.03050 | 41.030500 | 43.03050 | 40.55250 | 40.03050 |
| Surfactant Blend: Sodium Lauryl Sulfate Sodium Laureth Sulfate | 45.00000 | 45.00000 | 45.00000 | 45.00000 | 45.00000 |

TABLE 2-continued

SPLIT ENDS REPAIR WITH 2-IN-1 CONDITIONING SHAMPOO

| Ingredient Name | Sample 1 | Sample 2 | Sample 3 | Sample 4 | Sample 5 |
| --- | --- | --- | --- | --- | --- |
| Cocamidopropyl Betaine Acylglutamate (CS −22): CTFA: Sodium N-cocoyl L-Glutamate | 7.00000 | 7.00000 | 7.00000 | 7.00000 | 7.00000 |
| Foamtaine PPI-RC (45%) | — | 3.00000 | — | 3.00000 | 3.00000 |
| Polyderm PPI - SIWS | — | — | 1.00000 | 1.00000 | 1.00000 |
| Crotix Liquid: PEG-150 Pentaerythrityl Tetrastearate & PEG-6 Caprylic/capric glycerides and water | 0.75000 | 0.75000 | 0.75000 | 0.75000 | 0.75000 |
| Fragrance TCH −22117 | 0.75000 | 0.75000 | 0.75000 | 0.75000 | 0.75000 |
| Cocamide MEA | 2.00000 | 2.00000 | 2.00000 | 2.00000 | 2.00000 |
| Amphoteric Guar from National Starch: Carboxymethyl guar hydroxypropyl trimonium chloride | 0.25000 | 0.25000 | 0.25000 | — | 0.25000 |
| PEG −60 Almond Glycerides | 0.10000 | 0.10000 | 0.10000 | 0.10000 | 0.10000 |
| Methylparaben | 0.07500 | 0.07500 | 0.10000 | 0.07500 | 0.07500 |
| Kathon CG | 0.03000 | 0.03000 | 0.03000 | 0.03000 | 0.03000 |
| Tetrasodium EDTA | 0.01200 | 0.01200 | 0.01200 | 0.01200 | 0.01200 |
| Citric Acid | 0.00250 | 0.00250 | 0.00250 | 0.00250 | 0.00250 |
| % Split Ends Repair | 40.0% | 45.0% | 55.0% | 20.0% | 80.0% |

EXAMPLE 2
Hair Split End Repair with Betaine Based Polyurethane Surfactant, Silicone Polyurethane and Amphoteric Guar Procedure The procedure is the same as in Example 1. The total results are displayed in Table 3. below.

TABLE 3

SPLIT ENDS REPAIR WITH 2-IN-1 CONDITIONING SHAMPOO

| Ingredient Name | Sample 1 | Sample 2 | Sample 3 | Sample 4 | Sample 5 |
| --- | --- | --- | --- | --- | --- |
| Water | 43.03050 | 41.030500 | 43.03050 | 40.55250 | 40.03050 |
| Surfactant Blend: Sodium Lauryl Sulfate Sodium Laureth Sulfate | 45.00000 | 45.00000 | 45.00000 | 45.00000 | 45.00000 |
| Cocamidopropyl Betaine Acylglutamate (CS −22): CTFA: Sodium N-cocoyl L-Glutamate | 7.00000 | 7.00000 | 7.00000 | 7.00000 | 7.00000 |
| Foamtaine PPI-RC (45%) | — | 3.00000 | — | 3.00000 | 3.00000 |
| Polyderm PPI - SIWS | — | — | 1.00000 | 1.00000 | 1.00000 |
| Crotix Liquid: PEG-150 Pentaerythrityl Tetrastearate & PEG-6 Caprylic/capric glycerides and water | 0.75000 | 0.75000 | 0.75000 | 0.75000 | 0.75000 |
| Fragrance TCH −22117 | 0.75000 | 0.75000 | 0.75000 | 0.75000 | 0.75000 |
| Cocamide MEA | 2.00000 | 2.00000 | 2.00000 | 2.00000 | 2.00000 |
| Amphoteric Guar from National Starch: Carboxymethyl guar hydroxypropyl trimonium chloride | 0.25000 | 0.25000 | 0.25000 | — | 0.25000 |
| PEG −60 Almond Glycerides | 0.10000 | 0.10000 | 0.10000 | 0.10000 | 0.10000 |
| Methylparaben | 0.07500 | 0.07500 | 0.10000 | 0.07500 | 0.07500 |
| Kathon CG | 0.03000 | 0.03000 | 0.03000 | 0.03000 | 0.03000 |
| Tetrasodium EDTA | 0.01200 | 0.01200 | 0.01200 | 0.01200 | 0.01200 |
| Citric Acid | 0.00250 | 0.00250 | 0.00250 | 0.00250 | 0.00250 |

TABLE 3-continued

SPLIT ENDS REPAIR WITH 2-IN-1 CONDITIONING SHAMPOO

| Ingredient Name | Sample 1 | Sample 2 | Sample 3 | Sample 4 | Sample 5 |
|---|---|---|---|---|---|
| % Split Ends Repair (1 tress) per set | 50.0% | 50.0% | 40.0% | 35.0% | 78.0%* |

*One fiber was lost during the treatment.

EXAMPLE 3

Hair Split End Repair with Betaine Based Polyurethane Surfactant and Silicone Polyurethane with Amphoteric or Cationic Guar Procedure The procedure is the same as in Example 1. The total results are displayed in Table 4. below.

TABLE 4

SPLIT ENDS REPAIR WITH 2-IN-1 CONDITIONING SHAMPOO

| Ingredient Name | Sample 1 | Sample 2 | Sample 3 | Sample 4 | Sample 5 | Sample 6 |
|---|---|---|---|---|---|---|
| Water | 43.03050 | 41.030500 | 43.03050 | 40.55250 | 40.03050 | 40.03050 |
| Surfactant Blend | 45.00000 | 45.00000 | 45.00000 | 45.00000 | 45.00000 | 45.00000 |
| Aculglutamate (CS -22) | 7.00000 | 7.00000 | 7.00000 | 7.00000 | 7.00000 | 7.00000 |
| Foamtaine PPI-RC (45%) | — | 3.00000 | — | 3.00000 | 3.00000 | 3.00000 |
| Polyderm PPI - SIWS | — | — | 1.00000 | 1.00000 | 1.00000 | 1.00000 |
| Crotix Liquid | 0.75000 | 0.75000 | 0.75000 | 0.75000 | 0.75000 | 0.75000 |
| Fragrance TCH -22117 | 0.75000 | 0.75000 | 0.75000 | 0.75000 | 0.75000 | 0.75000 |
| Cocamide MEA | 2.00000 | 2.00000 | 2.00000 | 2.00000 | 2.00000 | 2.00000 |
| Cationic guar (Jaguar C-13S) | — | — | — | — | — | 0.25000 |
| Amphoteric Guar | 0.25000 | 0.25000 | 0.25000 | — | 0.25000 | — |
| PEG –60 Almond Glycerides | 0.10000 | 0.10000 | 0.10000 | 0.10000 | 0.10000 | 0.10000 |
| Methylparaben | 0.07500 | 0.07500 | 0.10000 | 0.07500 | 0.07500 | 0.07500 |
| Kathon CG | 0.03000 | 0.03000 | 0.03000 | 0.03000 | 0.03000 | 0.03000 |
| Tetrasodium EDTA | 0.01200 | 0.01200 | 0.01200 | 0.01200 | 0.01200 | 0.01200 |
| Citric Acid | 0.00250 | 0.00250 | 0.00250 | 0.00250 | 0.00250 | 0.00250 |
| % Split Ends Repair (1 tress) per set | 30.0% | 50.0% | 50.0% | 35.0% | 65.0% | 80.0% |

What is claimed is:

1. An aqueous hair conditioning composition comprising:

(a) a quaternary ammonium derivative of hydroxypropyl guar;

(b) a polymeric urethane betaine; and (c) a silicone polyurethane selected from the group consisting of polydimethyl siloxane—PEG ether/isophorone diisocyanate copolymer, polydimethyl siloxane—PEG ether/isophorone diisocyanate copolymer, and mixtures thereof.

2. The composition according to claim 1 wherein the quaternary ammonium derivative of hydroxypropyl guar is present in an amount of about 0.05% to about 5.0%, the polymeric urethane betaine is present in an amount of about 0.1% to about 30.0%, and the silicone polyurethane is present in an amount of about 0.1% to about 10.0%.

3. The composition according to claim 1 wherein the polymeric urethane betaine is selected from the group consisting of PEG-15 Cocamine bishydroxyethyl glycine/IPDI copolymer, PEG-13 soyamine bishydroxyethyl glycine/IPDI copolymer inner salt, and Bis-(Ricinoleamidopropyl dimethylamine polymer/IPDI N-carboxymethyl-N,N-dimethyl) hydroxide inner salt.

4. The composition according to claim 1 wherein the polymeric urethane betaine is present in an amount of about 0.1% to about 30.0%.

5. The composition according to claim 1 wherein the silicone polyurethane is present in an amount of about 0.1% to about 10.0%.

6. A method for repairing split ends of hair comprising contacting the hair with split ends with a composition comprising:

(a) a quaternary ammonium derivative of hydroxypropyl guar;

(b) a polymeric urethane betaine; and (c) a silicone polyurethane selected from the group consisting of polydimethyl siloxane—PEG ether/isophorone diisocyanate copolymer, polydimethyl siloxane—PEG ether/isophorone diisocyanate copolymer, and mixtures thereof.

7. The method according to claim 6 wherein the quaternary ammonium derivative of hydroxypropyl guar is present in an amount of about 0.05% to about 5.0%, the polymeric urethane betaine is present in an amount of about 0.1% to about 30.0%, and the silicone polyurethane is present in an amount of about 0.1% to about 10.0%.-

8. The method according to claim 7 wherein the polymeric urethane betaine is selected from the group consisting of PEG-15 Cocamine bishydroxyethyl glycine/IPDIcopolymer, PEG-13 soyamine bishydroxyethyl glycine/IPDI copolymer inner salt, and Bis-(Ricinoleamidopropyl dimethylamiine polymer/IPDI N-carboxymethyl-N,N-dimethyl) hydroxide inner salt.

9. The method according to claim 7 wherein the polymeric urethane betaine is present in an amount of about 0.1% to about 30.0%.

10. The method according to claim 7 wherein the silicone polyurethane is present in an amount of about 0.1% to about 10.0%.

\* \* \* \* \*